United States Patent
Su et al.

(10) Patent No.: US 6,664,238 B1
(45) Date of Patent: Dec. 16, 2003

(54) CARBAMATE AND CARBAZATE KETOLIDE ANTIBIOTICS

(75) Inventors: Wei-Guo Su, East Lyme, CT (US); Takushi Kaneko, Guilford, CT (US); Yong-Jin Wu, Madison, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/459,116

(22) Filed: Dec. 10, 1999

Related U.S. Application Data

(60) Provisional application No. 60/111,728, filed on Dec. 10, 1998.

(51) Int. Cl.[7] .................. A61K 31/70; A61P 31/04; C07H 17/08; C07D 421/00
(52) U.S. Cl. .................. 514/29; 514/339; 536/7.2; 536/7.4; 546/268.1
(58) Field of Search .................. 514/29, 339; 536/7.2, 536/7.4; 546/268.1

(56) References Cited

U.S. PATENT DOCUMENTS

| | | | |
|---|---|---|---|
| 4,474,768 A | 10/1984 | Bright | 424/180 |
| 4,517,359 A | 5/1985 | Kobrehel | 536/7.4 |
| 5,444,051 A | 8/1995 | Agouridas | 514/29 |
| 5,527,780 A | 6/1996 | Agouridas | 514/29 |
| 5,561,118 A | 10/1996 | Agouridas | 514/29 |
| 5,614,614 A | 3/1997 | Agouridas | 536/7.5 |
| 5,635,485 A | 6/1997 | Agouridas et al. | 514/29 |
| 5,656,607 A | 8/1997 | Agouridas | 514/29 |
| 5,747,467 A | 5/1998 | Agouridas et al. | 514/29 |
| 6,162,793 A * | 12/2000 | Agouridas et al. | 514/29 |
| 6,313,101 B1 * | 11/2001 | Denis et al. | 514/29 |
| 6,433,151 B1 * | 8/2002 | Denis et al. | 536/7.2 |

FOREIGN PATENT DOCUMENTS

| | | | | |
|---|---|---|---|---|
| EP | 0716093 B1 | 12/1996 | | |
| EP | 0716093 A1 | 10/1998 | | |
| EP | 1026170 | * | 9/2000 | |
| FR | 2732684 | | 4/1995 | |
| WO | 9800741 | | 1/1991 | |
| WO | 9803530 | | 1/1998 | |
| WO | 9823628 | | 4/1998 | |
| WO | 9838099 | | 9/1998 | |
| WO | 9925365 | | 5/1999 | |
| WO | 9921866 | | 6/1999 | |
| WO | WO9935157 | | 7/1999 | C07H/17/08 |

* cited by examiner

Primary Examiner—Richard L. Raymond
Assistant Examiner—Tamthom N. Truong
(74) Attorney, Agent, or Firm—Gregg C. Benson; Peter C. Richardson; Seth A. Jacobs

(57) ABSTRACT

This invention relates to compounds of the formula 1

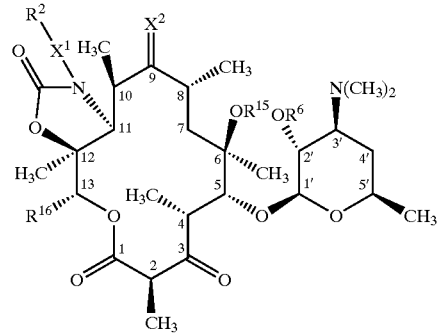

and to pharmaceutically acceptable salts and solvates thereof wherein $X^1$, $X^2$, $R^2$, $R^{15}$, $R^{16}$ and $R^6$ are as defined herein. The compounds of formula 1 are antibacterial and antiprotozoal agents that may be used to treat various bacterial and protozoal infections and disorders related to such infections. The invention also relates to pharmaceutical compositions containing the compounds of formula 1 and to methods of treating bacterial and protozoal infections by administering the compounds of formula 1.

10 Claims, No Drawings

CARBAMATE AND CARBAZATE KETOLIDE ANTIBIOTICS

This application claims benefit of provisional application Ser. No. 60/111,728 filed Dec. 10, 1998.

BACKGROUND OF THE INVENTION

This invention relates to novel macrolide compounds that are useful as antibacterial and antiprotozoal agents in mammals, including man, as well as in fish and birds. This invention also relates to pharmaceutical compositions containing the novel compounds and to methods of treating bacterial and protozoal infections in mammals, fish and birds by administering the novel compounds to mammals, fish and birds requiring such treatment.

Macrolide antibiotics are known to be useful in the treatment of a broad spectrum of bacterial and protozoal infections in mammals, fish and birds. Such antibiotics include various derivatives of erythromycin A such as azithromycin which is commercially available and is referred to in U.S. Pat. Nos. 4,474,768 and 4,517,359, both of which are incorporated herein by reference in their entirety. Other macrolide antibiotics are disclosed and claimed in PCT international application number PCT/IB98/00741, filed May 15, 1998, which designates the United States, U.S. Pat. No. 5,527,780, issued Jun. 18, 1996, and U.S. provisional application No. 60/101263 (filed Sep. 22, 1998). U.S. Pat. No. 5,527,780, PCT international application number PCT/IB98/00741, and U.S. provisional application No. 60/101263 are incorporated herein by reference in their entirety. Like azithromycin and other macrolide antibiotics, the novel macrolide compounds of the present invention possess activity against various bacterial and protozoal infections as described below.

SUMMARY OF THE INVENTION

The present invention relates to compounds of the formula

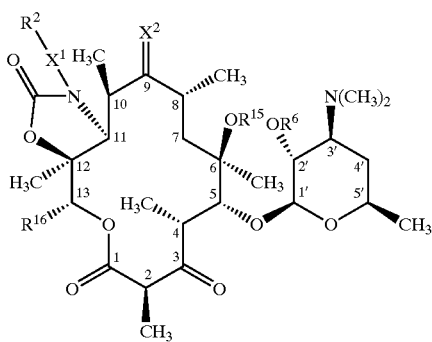

1 and to pharmaceutically acceptable salts and solvates thereof, wherein:

$X^1$ is O, —$CR^{13}R^{14}$— or —$NR^4$—;

$X^2$ is =O or =$NOR^1$;

$R^1$ is H, methyl or ethyl;

$R^2$ is —$C(R^7)(R^8)C(R^9)(R^{10})C(R^{11})(R^{12})$(4–10 membered heterocyclic) or —$(CR^7R^8)_r(C_3-C_7$ cycloalkylene)$(CR^9R^{10})_q$(4–10 membered heterocyclic), wherein q and r are each integers independently ranging from 0 to 2, and the heterocyclic moiety of the foregoing groups is substituted by —$(CR^4R^5)_t$(4–10 membered heterocyclic) or —$(CR^4R^5)_t(C_6-C_{10}$ aryl) wherein t is an integer from 0 to 5, and the aryl and heterocyclic moieties of each of the foregoing groups are optionally substituted by 1 to 4 $R^3$ groups;

each $R^3$ is independently selected from the group consisting of halo, cyano, nitro, trifluoromethyl, trifluoromethoxy, azido, —$C(O)R^5$, —$C(O)OR^5$, —$OC(O)R^5$, —$NR^5C(O)R^4$, —$C(O)NR^4R^5$, —$NR^4R^5$, hydroxy, $C_1-C_6$ alkyl, $C_2-C_6$ alkenyl, $C_2-C_6$ alkynyl, $C_6-C_{10}$ aryl, 4–10 membered heterocyclic, and $C_1-C_6$ alkoxy;

each $R^4$ and $R^5$ is independently selected from H and $C_1-C_6$ alkyl;

$R^6$ is H or —$C(O)(C_1-C_6$ alkyl);

$R^7$, $R^8$, $R^9$, $R^{10}$, $R^{11}$, $R^{12}$, $R^{13}$ and $R^{14}$ are each independently selected from H, halo and $C_1-C_8$ alkyl, provided that (a) where $X^1$ is —$CR^{13}R^{14}$— and $R^2$ is —$C(R^7)(R^8)C(R^9)(R^{10})C(R^{11})(R^{12})$(4–10 membered heterocyclic), at least one of $R^7$, $R^8$, $R^9$, $R^{10}$, $R^{11}$, $R^{12}$, $R^{13}$ and $R^{14}$ is halo or $C_1-C_6$ alkyl, and (b) where $X^1$ is —$NR^4$— and $R^2$ is —$C(R^7)(R^8)C(R^9)(R^{10})C(R^{11})(R^{12})$(4–10 membered heterocyclic), at least one of $R^7$, $R^8$, $R^9$, $R^{10}$, $R^{11}$, and $R^{12}$ is halo or $C_1-C_6$ alkyl;

or $R^7$ and $R^8$ are taken together with the carbon to which each is attached to form a $C_3-C_7$ cycloalkyl group and $R^9$, $R^{10}$, $R^{11}$, $R^{12}$, $R^{13}$ and $R^{14}$ are each independently selected from H, halo and $C_1-C_6$ alkyl;

or $R^9$ and $R^{10}$ are taken together with the carbon to which each is attached to form a $C_3-C_6$ cycloalkyl group and $R^7$, $R^8$, $R^{11}$, $R^{12}$, $R^{13}$ and $R^{14}$ are each independently selected from H, halo and $C_1-C_6$ alkyl;

or $R^{11}$ and $R^{12}$ are taken together with the carbon to which each is attached to form a $C_3-C_7$ cycloalkyl group and $R^7$, $R^8$, $R^9$, $R^{10}$, $R^{13}$ and $R^{14}$ are each independently selected from H, halo and $C_1-C_6$ alkyl;

$R^{15}$ is $C_1-C_6$ alkyl; and $R^{16}$ is H or $C_1-C_{10}$ alkyl.

Specific embodiments of the present invention include compounds of formula 1 wherein $X^2$ is =$NOR^1$, $R^{15}$ is methyl, $R^{16}$ is ethyl, $R^6$ is H or acetyl, $X^1$ is —$NR^4$— and $R^2$ is —$C(R^7)(R^8)C(R^9)(R^{10})C(R^{11})(R^{12})$(4–10 membered heterocyclic) wherein said heterocyclic group is substituted by 4–10 membered heterocyclic and the foregoing heterocyclic moieties are optionally substituted by 1 or 2 substituents independently selected from halo and $C_1-C_3$ alkyl. More specifically, $X^1$ is —NH— and $R^2$ is —$C(R^7)(R^8)C(R^9)(R^{10})C(R^{11})(R^{12})$(4-pyridin-3-yl-imidazol-1-yl), and (a) $R^7$, $R^8$, $R^9$ and $R^{10}$ are each H, $R^{11}$ is methyl or ethyl, and $R^{12}$ is H, methyl or ethyl; or (b) $R^7$, $R^8$, $R^{11}$ and $R^{12}$ are each H, $R^9$ is methyl or ethyl, and $R^{10}$ is H, methyl or ethyl; or (c) $R^9$, $R^{10}$, $R^{11}$ and $R^{12}$ are each H, $R^7$ is methyl or ethyl, and $R^8$ is H, methyl or ethyl.

Specific embodiments of the present invention include the following compounds:

11-Deoxy-5-O-desosaminyl-11-(3,3-dimethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(3(R)-methyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(3(R)-ethyll-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(3(S)-methyl-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(3(S)-ethyl-3-(4-pyridin-3-yl-imidazol-1-yl-propyl))hydrazo-6-O-methyl-3-oxoerythronolide A, 11,12carbamate, 9-E-(O-methyl)oxime;

11-Deoxy-5-O-desosaminyl-11-(2-(1-(4-pyridin-3-yl-imidazol-1-yl)-cyclopropyl)-ethyl)hydrazo-6-O-methyl-3-oxoerythronolide A, 11,12-carbamate, 9-E-(O-methyl)oxime;

11-Deoxy-5-O-desosaminyl-11-(2-(1-(4-pyridin-3-yl-imidazol-1-yl)-cyclobutyl)-ethyl)hydrazo-6-O-methyl-3-oxoerythronolide A, 11,12-carbamate, 9-E-(O-methyl)oxime;

11-Deoxy-5-O-desosaminyl-11-(2,2-dimethyl-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(2,2-diethyl-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(2,2-difluro-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(2,2-dichloro-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(2,2-dibromo-3(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(1-(4-pyridin-3-yl-imidazol-1-yl-methyl)-cyclopropyl)-methyl)hydrazo-6-O-methyl-3-oxoerythronolide A, 11,12-carbamate, 9-E-(O-methyl)oxime;

11-Deoxy-5-O-desosaminyl-11-(1-(4-pyridin-3-yl-imidazol-1-yl-methyl)-cyclobutyl)-methyl)hydrazo-6-O-methyl-3-oxoerythronolide A, 11,12-carbamate, 9-E-(O-methyl)oxime;

11-Deoxy-5-O-desosaminyl-11-(2(R)-methyl-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(2(R)-ethyl-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(2(S)-methyl-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(2(S)-ethyl-3-(4-pyridin-3-yl-imidazol-1-yl-propyl))hydrazo-6-O-methyl-3oxoerythronolide A, 11,12-carbamate, 9-E-(O-methyl)oxime;

11-Deoxy-5-O-desosaminyl-11-(2(R)-fluro-3-(4-pyridin-3-yl-imidazol-1-yl-propyl))hydrazo-6-O-methyl-3-oxoerythronolide A, 11,12-carbamate, 9-E-(O-methyl)oxime;

11-Deoxy-5-O-desosaminyl-11-(2(S)-flurol-3-(4-pyridin-3-yl-imidazol-1-yl-propyl))hydrazo-6-O-methyl-3-oxoerythronolide A, 11,12-carbamate, 9-E-(O-methyl)oxime;

and the pharmaceutically acceptable salts and solvates of the foregoing compounds.

The invention also relates to a pharmaceutical composition for the treatment of a bacterial infection or a protozoa infection, or a disorder related to a bacterial or protozoal infection, in a mammal, fish, or bird, which comprises a therapeutically effective amount of a compound of formula 1, or a pharmaceutically acceptable salt or solvate thereof, and a pharmaceutically acceptable carrier.

The invention also relates to a method of treating a bacterial infection or a protozoa infection, or a disorder related to a bacterial or protozoal infection, in a mammal, fish, or bird which comprises administering to said mammal, fish or bird a therapeutically effective amount of a compound of formula 1 or a pharmaceutically acceptable salt or solvate thereof.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, refers to the act of treating, as "treating" is defined immediately above.

As used herein, unless otherwise indicated, the terms or phrases "bacterial infection(s)", "protozoal infection(s)", and "disorders related to bacterial infections or protozoal infections" include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus, Enterococcus faecalis, E. faecium, E. casselflavus, S. epidermidis, S. haemolyticus,* or Peptostreptococcus spp.; pharyngitis, rheumatic fever, and glomerulonephritis related to infection by *Streptococcus pyogenes*, Groups C and G streptococci, *Corynebactelium diphtheriae*, or *Actinobacillus haemolyticum*; respiratory tract infections related to infection by *Mycoplasma pneumoniae, Legionella pneumophila, Streptococcus pneumoniae, Haemophilus influenzae,* or *Chlamydia pneumoniae*; blood and tissue infections, including endocarditis and osteomyelitis, caused by *S. aureus, S. haemolyticus, E. faecalis, E. faecium, E. durans*, including strains resistant to known antibacterials such as, but not limited to, beta-lactams, vancomycin, aminoglycosides, quinolones, chloramphenicol, tetracylines and macrolides; uncomplicated skin and soft tissue infections and abscesses, and puerperal fever related to infection by *Staphylococcus aureus*, coagulase-negative staphylococci (i.e., *S. epidermidis, S. hemolyticus*, etc.), *Streptococcus pyogenes, Streptococcus agalactiae*, Streptococcal groups C-F (minute-colony streptococci), viridans streptococci, *Corynebacterium minutissimum*, Clostridium spp., or *Bartonella henselae*; uncomplicated acute urinary tract infections related to infection by *Staphylococcus aureus*, coagulase-negative staphylococcal species, or Enterococcus spp.; urethritis and cervicitis; sexually transmitted diseases related to infection by *Chlamydia trachomatis, Haemophilus ducreyi, Treponema pallidum, Ureaplasma urealyticum,* or *Neiserria gonorrheae*; toxin diseases related to infection by *S. aureus* (food poisoning and toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes, H. influenzae,* or Listeria spp.; disseminated *Mycobacterium*

*avium* complex (MAC) disease related to infection by *Mycobacterium avium*, or *Mycobacterium intracellulare*; infections caused by *Mycobacterium tuberculosis, M. leprae, M. paratuberculosis, M. kansasii*, or *M. chelonei*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; and atherosclerosis or cardiovascular disease related to infection by *Helicobacter pylori* or *Chlamydia pneumoniae*. Bacterial infections and protozoal infections, and disorders related to such infections, which may be treated or prevented in animals include the following: bovine respiratory disease related to infection by *P. haemolytica, P. multocida, Mycoplasma bovis*, or Bordetella spp.; cow enteric disease related to infection by *E. coli* or protozoa (i.e., coccidia, cryptosporidia, etc.); dairy cow mastitis related to infection by *S. aureus, Strep. uberis, Streptococcus agalactiae, Streptococcus dysgalactiae*, Klebsiella spp., Corynebacterium, or Enterococcus spp.; swine respiratory disease related to infection by *A. pleuro., P. multocida*, or Mycoplasma spp.; swine enteric disease related to infection by *E. coli, Lawsonia intracellularis*, Salmonella, or *Serpulina hyodysinteriae*; cow footrot related to infection by Fusobacterium spp.; cow metritis related to infection by *E. coli*; cow hairy warts related to infection by *Fusobacterium necrophorum* or *Bacteroides nodosus*; cow pink-eye related to infection by *Moraxella bovis*; cow premature abortion related to infection by protozoa (i.e. neosporium); urinary tract infection in dogs and cats related to infection by *E. coli*; skin and soft tissue infections in dogs and cats related to infection by *S. epidermidis, S. intermedius*, coagulase neg. Staphylococcus or *P. multocida*; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. Other bacterial infections and protozoal infections, and disorders related to such infections, which may be treated or prevented in accord with the method of the present invention are referred to in J. P. Sanford et al., "The Sanford Guide To Antimicrobial Therapy," 26th Edition, (Antimicrobial Therapy, Inc., 1996).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having cyclic, straight and/or branched moieties. It is to be understood that to include cyclic moieties, the alkyl group must include at least 3 carbon atoms.

The term "alkenyl", as used herein, unless otherwise indicated, includes alkyl groups as defined above having at least one carbon-carbon double bond at some point in the alkyl chain.

The term "alkynyl", as used herein, unless otherwise indicated, includes alkyl groups as defined above having at least one carbon-carbon triple bond at some point in the alkyl chain.

The term "cycloalkylene", as used herein, unless otherwise indicated, includes divalent cycloalkyl groups.

The term "aryl", as used herein, unless otherwise indicated, includes an organic radical derived from an aromatic hydrocarbon by removal of one hydrogen, such as phenyl or naphthyl.

The term "4–10 membered heterocyclic", as used herein, unless otherwise indicated, includes aromatic and non-aromatic heterocyclic groups containing one or more heteroatoms each selected from O, S and N, wherein each heterocyclic group has from 4–10 atoms in its ring system. Non-aromatic heterocyclic groups include groups having only 4 atoms in their ring system, but aromatic heterocyclic groups must have at least 5 atoms in their ring system. The heterocyclic groups include benzo-fused ring systems and ring systems substituted with one or more oxo moieties. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula 1. The compounds of formula 1 that are basic in nature are capable of forming a wide variety of salts with various inorganic and organic acids. The acids that may be used to prepare pharmaceutically acceptable acid addition salts of such basic compounds of formula 1 are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula 1 that are acidic in nature, are capable of forming base salts with various pharmacologically acceptable cations. Examples of such salts include the alkali metal or alkaline earth metal salts and particularly, the sodium and potassium salts.

The present invention also includes all radiolabelled forms of the compounds of formula 1, and pharmaceutically acceptable salts thereof, wherein the radiolabel is selected from $^3$H, $^{11}$C and $^{14}$C. Such radiolabelled compounds are useful as research or diagnostic tools.

Certain compounds of formula 1 may have asymmetric centers and therefore exist in different enantiomeric forms.

This invention relates to the use of all optical isomers and stereoisomers of the compounds of formula 1 and mixtures thereof. In particular, the invention includes both the E and Z isomers of the —OR$^1$ group connected to the nitrogen of the oxime moiety at C-9 of the macrolide ring of formula 1.

DETAILED DESCRIPTION OF THE INVENTION

The preparation of the compounds of the present invention is illustrated in the following Schemes.

Scheme 1

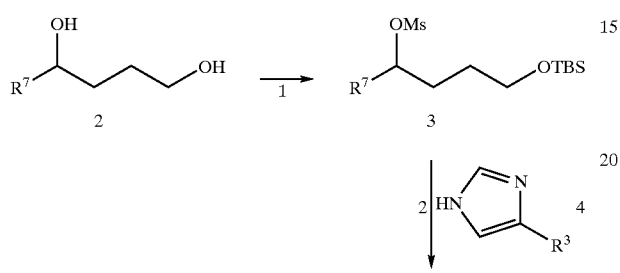

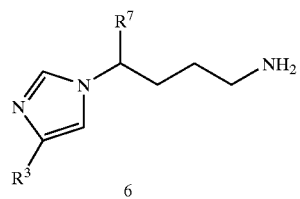

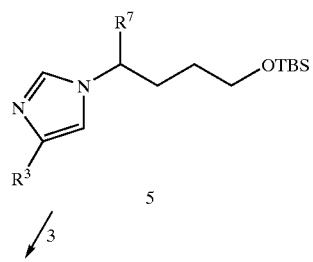

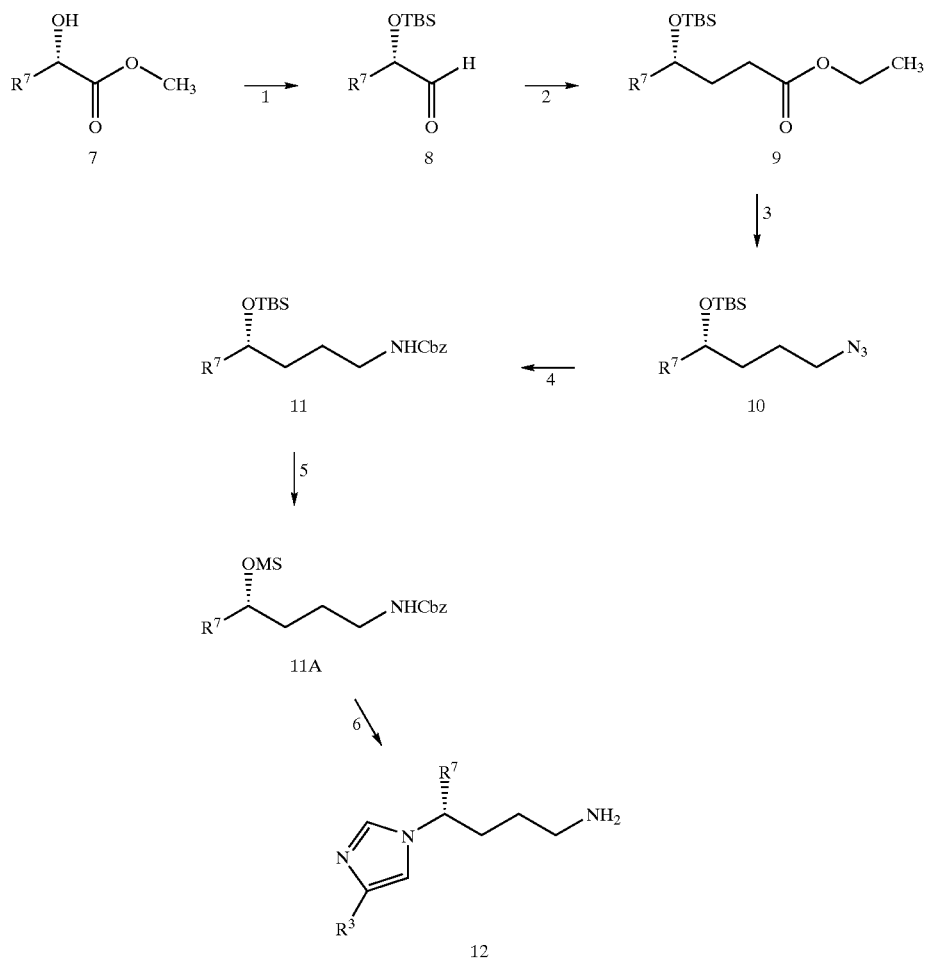

Scheme 2

Scheme 3
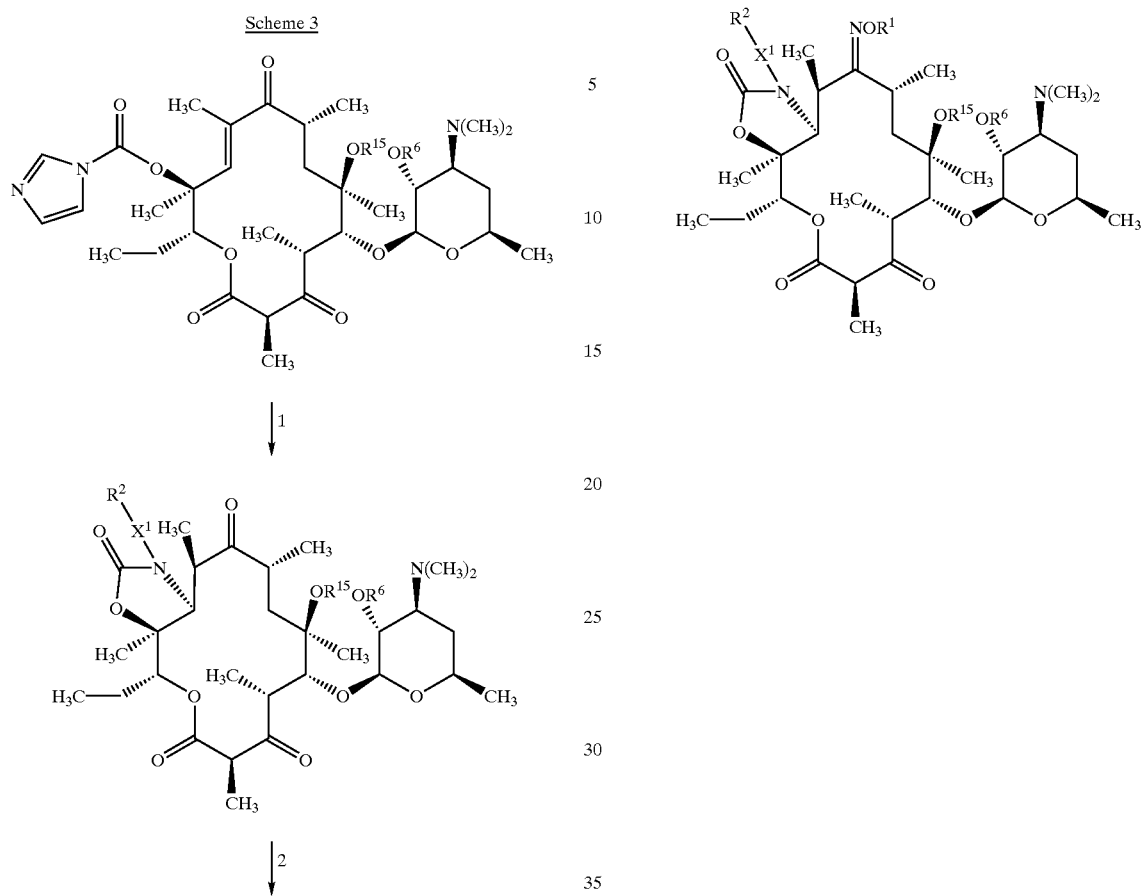
Scheme 4
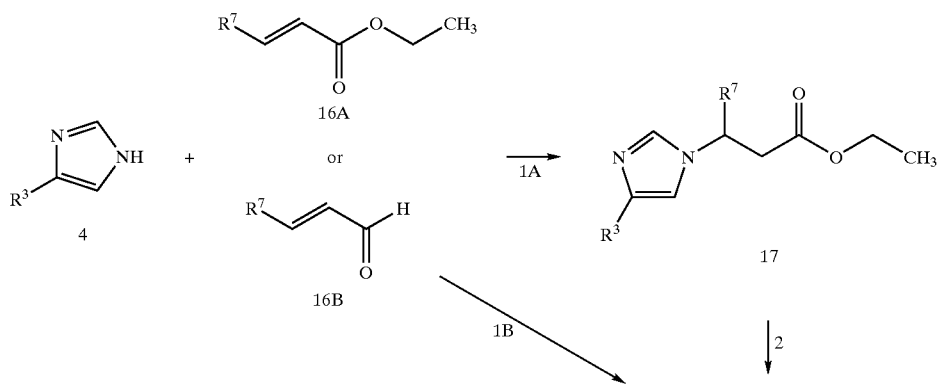

-continued
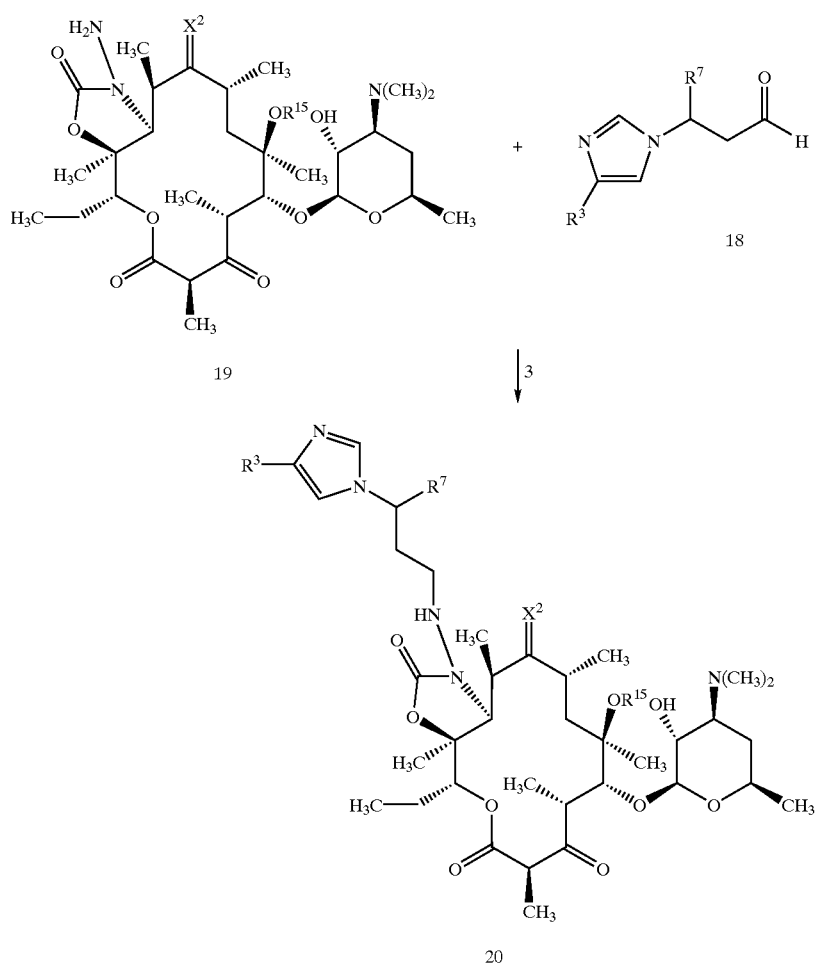
Scheme 5
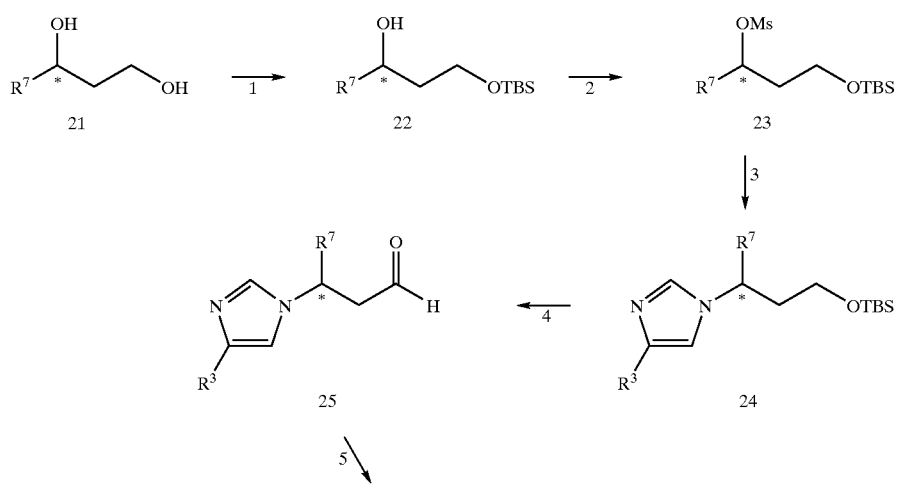

-continued
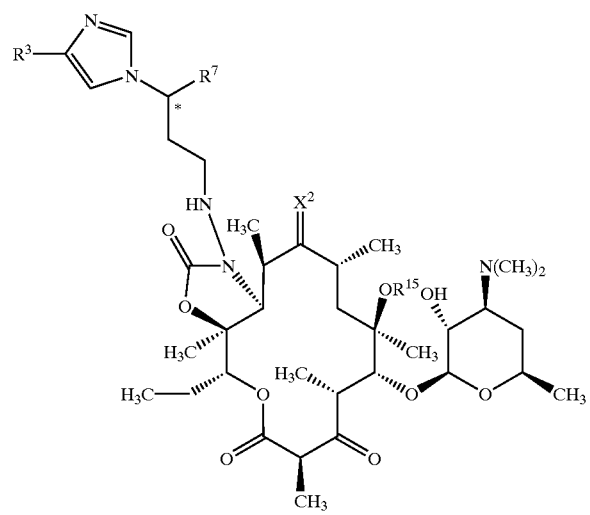
26
Scheme 6
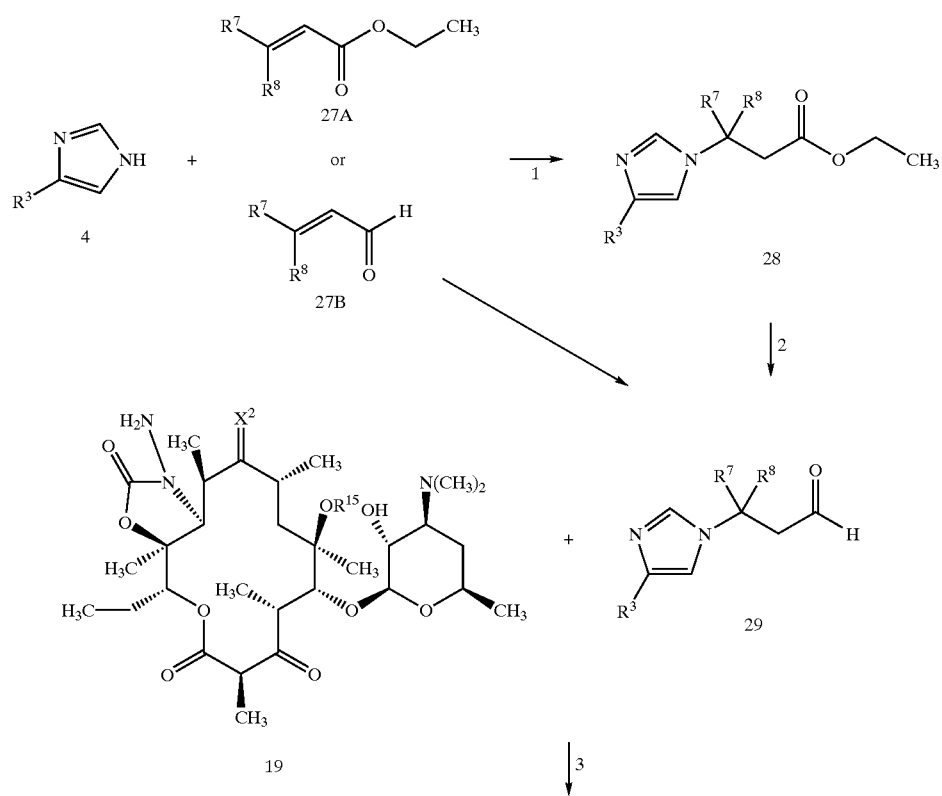

-continued

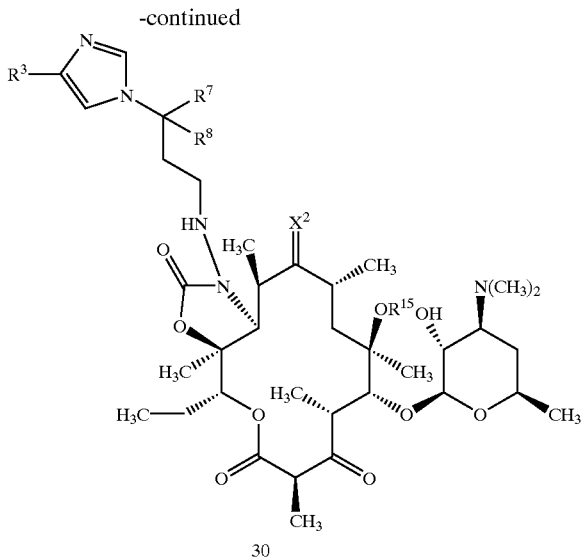

30

The preparation of the compounds of the present invention is illustrated in the above schemes. While the above Schemes illustrate the preparation of certain specific embodiments of the present invention, those skilled in the art would be able to prepare the full range of the claimed compounds using methods analogous to those illustrated above. The synthesis of racemic as well as enantiomerically pure side chains is illustrated in Schemes 1 and 2. In Scheme 1, the compound of formula 2, in which $R^7$ is an alkyl group as defined above, is commercially available or may be prepared according to methods familiar to those skilled in the art. Protection of the primary hydroxyl group as its t-butyldimethylsilyl ether (represented as OTBS in the compound of formula 3) may be done by treatment of the compound of formula 2 with 1 equivalent of t-butyldimethylsilyl chloride and imidazole in N,N-dimethylformamide (DMF) at room temperature (approximately 20–25° C). Conversion of the secondary alcohol to the corresponding mesylate of formula 3 (in which Ms represents the mesylate moiety) may be done by reaction with methanesulfonyl chloride and triethylamine in dichloromethane at approximately –20° C. Displacement of the mesylate with the compound of formula 4, wherein $R^3$ is as defined above, to provide the compound of formula 5 may be accomplished by reaction of the compound of formula 4 with a base such as sodium hydride or potassium carbonate at approximately 80° C. followed by addition of the mesylate compound of formula 3. The compound of formula 4 may be prepared according to methods familiar to those skilled in the art, including one or more synthetic methods described in H. Bredereck, R. Gompper, H. G. v. Schuh, and G. Theilig, *Angew. Chem.*, 24, 753 (1959). Deprotection of the silylether and conversion of the resultant alcohol to the amine of formula 6 may be achieved by the sequence: (1) treatment of the compound of formula 5 with tetrabutylammonium fluoride in tetrahydrofuran (THF) to provide the corresponding alcohol, (2) reaction of the alcohol with methanesulfonyl chloride and triethylamine to produce the mesylate, (3) displacement of the mesylate with sodium azide in DMF at room temperature to yield the primary azide, and (4) hydrogenation of the azide over palladium on carbon in methanol to provide the primary amine of formula 6. This compound may be introduced into the macrolide structure as the side chain represented as —$X^1$—$R^2$ in the compound of formula 1 according to the methods described herein and according to one or more methods described in U.S. Pat. No. 5,527,780 and PCT international application number PCT/IB98/00741, referred to above. Analogous side chains represented as —$X^1$—$R^2$ in the compound of formula 1 may be prepared in a similar manner.

While the side chain compounds prepared according to Scheme 1 are racemic, those prepared according to Scheme 2 are substantially enantiomerically pure. With reference to Scheme 2, the enantiomerically pure compound of the formula 7, which is commercially available, such as S-(–)-methyl lactate, or prepared according to methods familiar to those skilled in the art, may be converted to its t-butyldimethylsilyl ether by treatment with t-butyldimethylchlorosilane in DMF in the presence of imidazole at a temperature ranging from 0° C. to 40° C., preferably at room temperature. Reduction of this compound with di-isobutylaluminum hydride in toluene at approximately –70° C. provides the aldehyde of formula 8 (wherein TBS represents t-butyldimethylsilyl). Wittig coupling of the compound of formula 8 with carbethoxymethylene triphenylphosphorane in benzene at a temperature ranging from 60° C. to 80° C. produces the corresponding unsaturated ester which may be hydrogenated over palladium in ethyl acetate to provide the ester of formula 9. Reduction of the ester to the corresponding alcohol using lithium aluminum hydride in THF, conversion of the alcohol to the corresponding mesylate by treatment with methanesulfonyl chloride and triethylamine in dichloromethane at a temperature ranging from –20° C. to 0° C., and, finally, displacement of the mesyl group with azide by reaction with sodium azide in DMF at room temperature affords the azide of formula 10. Hydrogenation of the compound of formula 10 over palladium in a polar solvent, such as methanol, followed by reaction with benzylchloroformate provides the benzyloxycarbonyl amide of formula 11 (wherein Cbz represents benzyloxycarbonyl). Desilylation with tetra-n-butylammonium fluoride in THF followed by treatment with methanesulfonyl chloride and triethylamine at a temperature ranging from –20° C. to 0° C. produces the corresponding mesylate of formula 11A (wherein Ms represents methanesulfonyl). Reaction of the compound of formula 11A with a compound of the formula 4 (which is illustrated in Scheme 1) and sodium hydride in dry DMF at a temperature ranging from 20° C. to 100° C., followed by deprotection by hydrogenation over a palladium catalyst in methanol at room temperature, provides a compound of the formula 12. An example of a compound corresponding to formula 12 is (R)-4-(4-pyridin-3-yl-imidazol-1-yl)-pentylamine. Following the same procedures outlined above except starting with a compound having the opposite stereochemical orientation with respect to the hydroxy group, such as R-(+)-methyl lactate, provides a compound corresponding to the compound of formula 12 except the stereochemical orientation of the $R^7$ group is opposite to that illustrated for the compound of formula 12. An example of such a compound is (S)-4-(4-pyridin-3-yl-imidazol-1-yl)-pentylamine.

The synthesis of the final ketolide is illustrated in Scheme 3. The compound of formula 13, wherein $R^6$ is acetyl, may be prepared as described in U.S. Pat. No. 5,543,400 (issued Aug. 6, 1996). In general, the intermediate compound of formula 14 may be prepared as described in U.S. Pat. 5,543,400, PCT international application number PCT/IB98/00741 and U.S. Pat. 5,527,780, each of which is referred to above, and also United Kingdom patent application number 2,288,174 (published Oct. 11, 1995), and G. Griesgraber et al., "3-Keto-11,12-carbazate Derivatives of 6-O-Methylerythromycin A," Journal of Antibiotics, 49(5), 465–477 (1996).

In step 1 of Scheme 3, compounds of the formula 14, wherein $R^6$ is H, $X^1$ is —$CH_2$— and $R^2$ and $R^3$ are as defined above, may be prepared by treating a compound of the formula 13 with a compound of the formula $H_2N$—$X^1$—$R^2$, wherein $X^1$ is —$CH_2$— and $R^2$ is as defined above, in a solvent such as acetonitrile, DMF, THF, dimethoxy ethane or dimethylsulfoxide (DMSO), preferably acetonitrile, at a temperature within the range of about 50° C. to 90° C., preferably about 80° C., for a period of about 4 to 16 hours. Compounds of the formula 14, wherein $X^1$ is —NH— and $R^2$ is as defined above, can be prepared as described below in reference to schemes 4–6 and further as described in United Kingdom patent application number 2,288,174, referred to above. In step 2 of Scheme 3, compounds of the formula 15 may be prepared by treating a compound of the formula 14 with a compound of the formula $R^1ONH_2.HCl$ or $R^1ONH_2$, wherein $R^1$ is as defined above, in the presence of an acid, such as Py.HCl (wherein Py denotes pyridine) or $Et_3N.HCl$ (wherein Et denotes ethyl), in a polar solvent, preferably methanol, ethanol, or isopropyl alcohol, at a temperature within the range of about 65° C. to 95° C. for a period of about 10 hours to 6 days.

Scheme 4 illustrates the preparation of compounds of formula 1 wherein $X^1$ is —NH— and $R^2$ is as defined above. In particular, Scheme 4 illustrates an $R^2$ moiety wherein "n" is 2, although groups wherein "n" has other values may be used following an analogous procedure. In the compounds illustrated in Scheme 4, $R^7$ is an alkyl group and $R^8$ (not shown) is H. In step 1 of Scheme 4, a compound of formula 16A is treated with a compound of formula 4 in THF at room temperature to provide the compound of formula 17. Reduction with diisobutylaluminum hydride in dichloromethane at approximately −70° C. provides the aldehyde of formula 18. In the alternative, compound 18 may be obtained by treating a compound of formula 16B with a compound of formula 4 in the presence of an acid in THF or DMF at 20–100° C. The preferred acids are acetic acid, p-toluenesulfonic acid, and pyridinium p-toluenesulfonate. The compound of formula 19, wherein $X^2$ is as defined above, may be prepared as described in PCT international application number PCT/IB98/00741 and U.S. Pat. No. 5,527,780, referred to above. Further, the synthesis of 11,12-cyclic carbazates analogous to the compounds of formula 19 is described in W. R. Baker, J. D. Clark, R. L. Stephens, and K. H. Kim, J. Org. Chem., 53, 2340 (1988). Condensation of the aldehyde of formula 18 with the compound of formula 19 in toluene at approximately 100° C. followed by reduction of the resultant imine in methanol with sodium cyanoborohydride at 23° C. gave rise to the compound of formula 20 wherein the product is racemic with respect to the chiral carbon to which $R^7$ is attached.

Scheme 5 illustrates the preparation of compounds that are similar to those of formula 20 except the product is substantially enantiomerically pure with respect to the chiral carbon to which $R^7$ is attached. This is indicated in structures 21–26 in Scheme 5 wherein the asterisk represents a specific stereoisomeric orientation (specifically, R or S) with respect to the carbon to which $R^7$ is attached. In the compounds illustrated in Scheme 5, $R^7$ is an alkyl group and $R^8$ (not shown) is H. The synthesis of these compounds begins with chiral starting materials, which are illustrated here as R- or S-1,3-butanediol (the compound of formula 21). Monosilylation by reaction with 1 equivalent of t-butyldimethylsilyl chloride in DMF in the presence of imidazole at room temperature, about 23° C., for about 12 hours provides mono-silyl ether (the compound of formula 22 wherein TBS is t-butyldimethylsilyl). Mesylation by treatment with 1 equivalent of methanesulfonyl chloride and triethylamine in dichloromethane at approximately −20° C. for approximately 40 minutes provides the corresponding mesylate of formula 23 (wherein Ms denotes the mesylate moiety). Displacement of the mesylate with a compound of formula 4 (illustrated in Scheme 1) in DMF with sodium hydride provides the compound of formula 24 with complete inversion of the stereochemistry of the alpha $R^7$ group. Desilylation by reaction with tetra-t-butylammonium fluoride in THF followed by swern oxidation with oxalyl chloride and DMSO provides the chiral alpha-$R^7$ imidazole propionaldehyde of formula 25. Coupling of the aldehyde with the cyclic carbazate of formula 19, as described in reference to Scheme 4 above, provides the R—$R^7$ or S—$R^7$ compound of formula 26.

Scheme 6 illustrates the preparation of compounds of formula 26 which are similar to those of formula 20 except that both $R^7$ and $R^8$ are alkyl groups. The synthesis illustrated in Scheme 6 follows the same general steps and conditions of the synthesis illustrated in Scheme 4. As in Scheme 4, compound 29 may be obtained by reacting compounds 27A and 4 to generate compound 28 which may be treated to obtain compound 29, or by treating a compound of formula 27B with a compound of formula 4 in the presence of an acid in THF or DMF at 20–100° C. The starting materials are either commercially available or they may be prepared according to synthetic methods familiar to those skilled in the art.

The compounds of the present invention may have asymmetric carbon atoms. Such diastereomeric mixtures can be separated into their individual diastereomers on the basis of their physical chemical differences by methods known to those skilled in the art, for example, by chromatography or fractional crystallization. Enantiomers can be separated by converting the enantiomeric mixtures into a diastereomeric mixture by reaction with an appropriate optically active compound (e.g., alcohol), separating the diastereomers and converting (e.g., hydrolyzing) the individual diastereomers to the corresponding pure enantiomers. All such isomers, including diastereomeric mixtures and pure enantiomers are considered as part of the invention.

The compounds of formula 1 that are basic in nature are capable of forming a wide variety of different salts with various inorganic and organic acids. Although such salts must be pharmaceutically acceptable for administration to animals, it is often desirable in practice to initially isolate the compound of formula 1 from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained. The desired acid salt can also be precipitated from a solution of the free base in an organic solvent by adding to the solution an appropriate mineral or organic acid.

Those compounds of the formula 1 that are acidic in nature are capable of forming base salts with various pharmacologically acceptable cations. Examples of such salts include the alkali metal or alkaline-earth metal salts and particularly, the sodium and potassium salts. These salts may be prepared by conventional techniques. The chemical bases which are used as reagents to prepare the pharmaceutically acceptable base salts of this invention are those which form non-toxic base salts with the acidic compounds of formula 1. Such non-toxic base salts include those derived from such pharmacologically acceptable cations as sodium, potassium calcium and magnesium, etc. These salts can be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum yields of the desired final product.

The activity of the compounds of the present invention against bacterial and protozoa pathogens is demonstrated by the compound's ability to inhibit growth of defined strains of human (Assay I) or animal (Assays II and III) pathogens.

Assay I

Assay I, described below, employs conventional methodology and interpretation criteria and is designed to provide direction for chemical modifications that may lead to compounds that circumvent defined mechanisms of macrolide resistance. In Assay I, a panel of bacterial strains is assembled to include a variety of target pathogenic species, including representatives of macrolide resistance mechanisms that have been characterized. Use of this panel enables the chemical structure/activity relationship to be determined with respect to potency, spectrum of activity, and structural elements or modifications that may be necessary to obviate resistance mechanisms. Bacterial pathogens that comprise the screening panel are shown in the table below. In many cases, both the macrolide-susceptible parent strain and the macrolide-resistant strain derived from it are available to provide a more accurate assessment of the compound's ability to circumvent the resistance mechanism. Strains that contain the gene with the designation of ermA/ermB/ermC are resistant to macrolides, lincosamides, and streptogramin B antibiotics due to modifications (methylation) of 23S rRNA molecules by an Erm methylase, thereby generally prevent the binding of all three structural classes. Two types of macrolide efflux have been described; msrA encodes a component of an efflux system in staphylococci that prevents the entry of macrolides and streptogramins while mefA/E encodes a transmembrane protein that appears to efflux only macrolides. Inactivation of macrolide antibiotics can occur and can be mediated by either a phosphorylation of the 2'-hydroxyl (mph) or by cleavage of the macrocyclic lactone (esterase). The strains may be characterized using conventional polymerase chain reaction (PCR) technology and/or by sequencing the resistance determinant. The use of PCR technology in this application is described in J. Sutcliffe et al., "Detection Of Erythromycin-Resistant Determinants By PCR", Antimicrobial Agents and Chemotherapy, 40(11), 2562–2566 (1996). The assay is performed in microtiter trays and interpreted according to *Performance Standards for Antimicrobial Disk Susceptibility Tests—Sixth Edition: Approved Standard*, published by The National Committee for Clinical Laboratory Standards (NCCLS) guidelines; the minimum inhibitory concentration (MIC) is used to compare strains. Compounds are initially dissolved in dimethylsulfoxide (DMSO) as 40 mg/ml stock solutions.

| Strain Designation | Macrolide Resistance Mechanism(s) |
| --- | --- |
| *Staphylococcus aureus* 1116 | susceptible parent |
| *Staphylococcus aureus* 1117 | ermB |
| *Staphylococcus aureus* 0052 | susceptible parent |
| *Staphylococcus aureus* 1120 | ermC |
| *Staphylococcus aureus* 1032 | msrA, mph, esterase |
| *Staphylococcus hemolyticus* 1006 | msrA, mph |
| *Streptococcus pyogenes* 0203 | susceptible parent |
| *Streptococcus pyogenes* 1079 | ermB |
| *Streptococcus pyogenes* 1062 | susceptible parent |
| *Streptococcus pyogenes* 1061 | ermB |
| *Streptococcus pyogenes* 1064 | ermB |
| *Streptococcus agalactiae* 1024 | susceptible parent |
| *Streptococcus agalactiae* 1023 | ermB |
| *Streptococcus pneumoniae* 1016 | susceptible |
| *Streptococcus pneumoniae* 1046 | ermB |
| *Streptococcus pneumoniae* 1095 | ermB |
| *Streptococcus pneumoniae* 1175 | mefE |
| *Streptococcus pneumoniae* 0085 | susceptible |
| *Haemophilus influenzae* 0131 | susceptible |
| *Moraxella catarrhalis* 0040 | susceptible |
| *Moraxella catarrhalis* 1055 | erythromycin intermediate resistance |
| *Escherichia coli* 0266 | susceptible |

Assay II is utilized to test for activity against *Pasteurella multocida* and Assay III is utilized to test for activity against *Pasteurella haemolytica*.

Assay II

This assay is based on the liquid dilution method in microliter format. A single colony of *P. multocida* (strain 59A067) is inoculated into 5 ml of brain heart infusion (BHI) broth. The test compounds are prepared by solubilizing 1 mg of the compound in 125 μl of dimethylsulfoxide (DMSO). Dilutions of the test compound are prepared using uninoculated BHI broth. The concentrations of the test compound used range from 200 μg/ml to 0.098 μg/ml by two-fold serial dilutions. The *P. multocida* inoculated BHI is diluted with uninoculated BHI broth to make a $10^4$ cell suspension per 200 μl. The BHI cell suspensions are mixed with respective serial dilutions of the test compound, and incubated at 37° C. for 18 hours. The minimum inhibitory concentration (MIC) is equal to the concentration of the compound exhibiting 100% inhibition of growth of *P. multocida* as determined by comparison with an uninoculated control.

Assay III

This assay is based on the agar dilution method using a Steers Replicator. Two to five colonies isolated from an agar plate are inoculated into BHI broth and incubated overnight at 37° C. with shaking (200 rpm). The next morning, 300 μl of the fully grown *P. haemolytica* preculture is inoculated into 3 ml of fresh BHI broth and is incubated at 37° C. with shaking (200 rpm). The appropriate amounts of the test compounds are dissolved in ethanol and a series of two-fold serial dilutions are prepared. Two ml of the respective serial dilution is mixed with 18 ml of molten BHI agar and solidified. When the inoculated *P. haemolytica* culture reaches 0.5 McFarland standard density, about 5 μl of the *P. haemolytica* culture is inoculated onto BHI agar plates containing the various concentrations of the test compound using a Steers Replicator and incubated for 18 hours at 37° C. Initial concentrations of the test compound range from 100–200 μg/ml. The MIC is equal to the concentration of the test compound exhibiting 100% inhibition of growth of *P. haemolytica* as determined by comparison with an uninoculated control.

The in vivo activity of the compounds of formula 1 can be determined by conventional animal protection studies well known to those skilled in the art, usually carried out in mice.

Mice are allotted to cages (10 per cage) upon their arrival, and allowed to acclimate for a minimum of 48 hours before being used. Animals are inoculated with 0.5 ml of a 3×10$^3$ CFU/ml bacterial suspension (*P. multocida* strain 59A006) intraperitoneally. Each experiment has at least 3 non-medicated control groups including one infected with 0.1× challenge dose and two infected with 1× challenge dose; a 10× challenge data group may also be used. Generally, all mice in a given study can be challenged within 30–90 minutes, especially if a repeating syringe (such as a Cornwall® syringe) is used to administer the challenge. Thirty minutes after challenging has begun, the first compound treatment is given. It may be necessary for a second person to begin compound dosing if all of the animals have not been challenged at the end of 30 minutes. The routes of administration are subcutaneous or oral doses. Subcutaneous doses are administered into the loose skin in the back of the neck whereas oral doses are given by means of a feeding needle. In both cases, a volume of 0.2 ml is used per mouse. Compounds are administered 30 minutes, 4 hours, and 24 hours after challenge. A control compound of known efficacy administered by the same route is included in each test. Animals are observed daily, and the number of survivors in each group is recorded. The *P. multocida* model monitoring continues for 96 hours (four days) post challenge.

The PD$_{50}$ is a calculated dose at which the compound tested protects 50% of a group of mice from mortality due to the bacterial infection which would be lethal in the absence of drug treatment.

The compounds of formula 1, and the pharmaceutically acceptable salts and solvates thereof (hereinafter "the active compounds"), may be adminstered through oral, parenteral, topical, or rectal routes in the treatment or prevention of bacterial or protozoa infections. In general, these compounds are most desirably administered in dosages ranging from about 0.2 mg per kg body weight per day (mg/kg/day) to about 200 mg/kg/day in single or divided doses (i.e., from 1 to 4 doses per day), although variations will necessarily occur depending upon the species, weight and condition of the subject being treated and the particular route of administration chosen. However, a dosage level that is in the range of about 4 mg/kg/day to about 50 mg/kg/day is most desirably employed. Variations may nevertheless occur depending upon the species of mammal, fish or bird being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effects, provided that such larger doses are first divided into several small doses for administration throughout the day.

The active compounds may be administered alone or in combination with pharmaceutically acceptable carriers or diluents by the routes previously indicated, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the active compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral adinistration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

Additionally, it is also possible to administer the active compounds of the present invention topically and this may be done by way of creams, jellies, gels, pastes, patches, ointments and the like, in accordance with standard pharmaceutical practice.

For administration to animals other than humans, such as cattle or domestic animals, the active compounds may be administered in the feed of the animals or orally as a drench composition.

The active compounds may also be adminstered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The active compounds may also be coupled with soluble polymers as targetable drug carriers. Such polymers can include polyvinylpyrrolidone, pyran copolymer, polyhydroxypropylmethacrylamide phenyl, polyhydroxyethylaspartamide-phenol, or polyethyleneoxide-polylysine substituted with palmitoyl-residues. Furthermore, the active compounds may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

The Examples provided below illustrate specific embodiments of the invention, but the invention is not limited in scope to the Examples specifically exemplified.

The Examples provided below illustrate specific embodiments of the invention, but the invention is not limited in scope to the Examples specifically exemplified.

responding R-methyl isomer of formula 32 (below), wherein $X^2$ is O, Y is H, and $X^1$ is —CH$_2$—, was produced in similar yield.

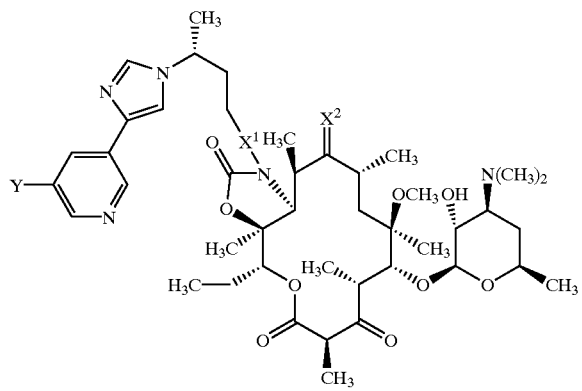

EXAMPLE 3

Following the procedure described in Example 1, using (S)4-(4-pyridin-3-yl-imidazol-1-yl)-pentylamine, the corresponding S-methyl isomer of formula 33 (below), wherein $X^2$ is O, Y is H, and $X^1$ is —CH$_2$—, was produced in similar yield.

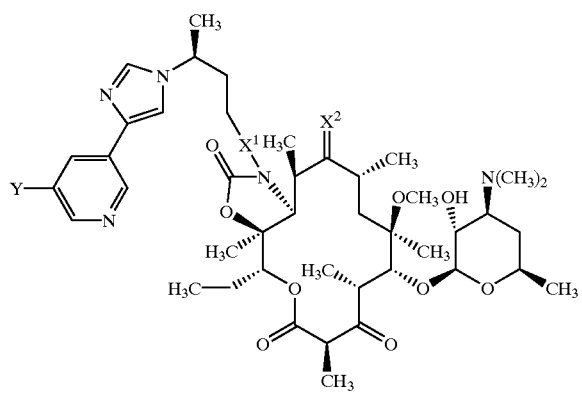

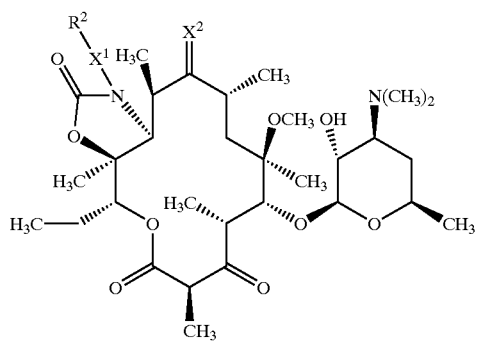

EXAMPLE 1

To a solution of the allylic acylimidazole (0.95 g) of formula 13 in acetonitrile (6 ml) and THF (3 ml) was added (R/S)-4-(4-pyridin-3-yl-imidazol-1-yl)-pentylamine (0.624 g). The resulting solution was heated to reflux under nitrogen for 24 hours. Solvents were removed in vacuo and pumped to dryness. The resulting foam was re-suspended into methanol (10 ml) and heated under reflux for 5 hours. After cooling to room temperature (20–25° C.), the mixture was poured into 5% sodium carbonate solution and extracted with dichloromethane (3×50 ml). Drying over potassium carbonate, filtration, concentration and purification by silica-gel chromatography (SGC) provided the compound of formula 31 illustrated above wherein —$X^1$—$R^2$ is (R/S)4-(4-pyridin-3-yl-imidazol-1-yl)pentyl and $X^2$ is O. Yields ranged between 40 and 60%.

EXAMPLE 2

Following the procedure described in Example 1, using (R)-4-(4-pyridin-3-yl-imidazol-1-yl)-pentylamine, the cor-

EXAMPLE 4

Following the procedure described in Example 1, using (R)-4-[4-(5-fluoro)-pyridin-3-yl-imidazol-1-yl]-pentylamine (which may be prepared as described in E. P. Kyba, S. Liu, K. Chockalingam, B. R. Ready, *J. Org. Chem.*, 53, 3513 (1988)), the corresponding R-methyl isomer of formula 32 (above), wherein $X^2$ is O, Y is fluoro, and $X^1$ is —CH$_2$—, is produced.

EXAMPLE 5

Following the procedures described in Example 1, using (S)-4-[4-(5-fluoro)-pyridin-3-yl-imidazol-1-yl]-pentylamine (which may be prepared as described in E. P. Kyba, S. Liu, K. Chockalingam, B. R. Ready, *J. Org. Chem.*, 53, 3513 (1988)), the corresponding S-methyl isomer of formula 33 (above), wherein $X^2$ is O, Y is fluoro, and $X^1$ is —CH$_2$—, is produced.

EXAMPLE 6

The compound produced in Example 1 (100 mg) is dissolved in ethanol (2 ml). To this is added methoxylamine hydrochloride (50 mg). The resulting mixture is heated under reflux for 3 days. The mixture is diluted with water, and pH is adjusted to 9.5 with 1 N sodium hydroxide. Extraction with dichloromethane (3×25 ml), drying over potassium carbonate, concentration, and SGC purification results in the compound of formula 31, illustrated above, wherein —$X^1$—$R^2$ is (R/S)-4-(4-pyridin-3-yl-imidazol-1-yl)pentyl and $X^2$ is =$NOCH_3$.

EXAMPLE 7

Following the procedure of Example 6, using the compounds of Examples 2 through 5 as starting materials, compounds are obtained wherein —$X^1$—$R^2$ corresponds to that of Examples 2–5 and $X^2$ is =$NOCH_3$.

EXAMPLE 8

To a solution of the compound of formula 19 (wherein $X^2$ is O)(see Scheme 4 above) (82 mg) in toluene (1 ml) was added 3-(R/S)-4-(4-pyridin-3-yl-imidazol-1-yl)-butyraldehyde (40 mg). The mixture was heated at 110° C. for 12 hours. Solvent was removed and the resulting foam was re-suspended in methanol (5 ml). To it was added acetic acid (0.047 ml) and sodium cyanoborohydride (25 mg). After stirring for 12 hours, water was added and the pH was adjusted to 2 with 1N HCl. The mixture was stirred for 30 minutes and the pH was adjusted to 9.5 with 1N sodium hydroxide. Extraction with dichloromethane (3×25 ml), drying over potassium carbonate, filtration, concentration and SGC purification using 3% methanol-dichloromethane containing 0.3% concentrated ammonium hydroxide as eluent provided a compound of formula 31, illustrated above, wherein —$X^1$—$R^2$ is (R/S)-3-(4-pyridin-3-yl-imidazol-1-yl)-butylamino and $X^2$ is O (67 mg).

EXAMPLE 9

Following the procedures described in Example 8, using the compound of formula 19 (wherein $X^2$ is =$NOCH_3$), the corresponding compound of of formula 31, illustrated above, wherein —$X^1$—$R^2$ is (R/S)-3-(4-pyridin-3-yl-imidazol-1-yl)-butylamino and $X^2$ is =$NOCH_3$, was prepared in a yield similar to that found for the product of Example 8.

EXAMPLE 10

Following the procedures described in Example 8, using 3-(R)-4-(4-pyridin-3-yl-imidazol-1-yl)-butyraldehyde and the compound of formula 19 wherein $X^2$ is =O as starting materials, the compound of of formula 32 (above), wherein $X^2$ is O, Y is H, and $X^1$ is NH, was obtained.

EXAMPLE 11

Following the procedures described in Example 8, using 3-(R)4-(4-pyridin-3-yl-imidazol-1-yl)-butyraldehyde and the compound of formula 19 wherein $X^2$ is =$NOCH_3$ as starting materials, the compound of of formula 32 (above), wherein $X^2$ is =$NOCH_3$, Y is H, and $X^1$ is NH, was obtained.

EXAMPLE 12

Following the procedures described in Example 8, using 3-(S)-4-(4-pyridin-3-yl-imidazol-1-yl)-butyraldehyde and the compound of formula 19 wherein $X^2$ is =O as starting materials, the compound of of formula 33 (above), wherein $X^2$ is O, Y is H, and $X^1$ is NH, was obtained.

EXAMPLE 13

Following the procedures described in Example 8, using 3-(S)4-(4-pyridin-3-yl-imidazol-1-yl)-butyraldehyde and the compound of formula 19 wherein $X^2$ is =$NOCH_3$ as starting materials, the compound of of formula 33 (above), wherein $X^2$ is =$NOCH_3$, Y is H, and $X^1$ is NH, was obtained.

EXAMPLE 14

2-Methyl-3-(4-pyridin-3-yl-imidazol-1-yl)-propioaldehyde

To a solution of 4-pyridin-3-yl-imidazole (8.5 g) in THF (tetrahydrofuran) (293 mL) was added acetic acid (16.8 mL) and methacrolein (9.7 mL) and the resulting solution was heated under gentle reflux for 24 hours. Another 9.7 mL methacrolein was added and the solution was heated under reflux for another 24 hours. THF was then removed in vacuo and the residue was purified on a Flash 75 long column eluting with MeOH—$CH_2Cl_2$ to give the title compound as slightly yellow oil.

MS: m/z 215 (M+H).

EXAMPLE 15

3,3-Dimethyl-3-(4-pyridin-3-yl-imidazol-1-yl)-propioaldehyde

To a solution of 4-pyridin-3-yl-imidazole (1 g) in THF (34 mL) was added acetic acid (1.6 mL) and 3-methyl-2-butenal (3.3 mL) and the resulting solution was heated under gentle reflux for 24 hours. THF was then removed in vacuo and the residue was purified on a Flash 75 long column eluting with MeOH—$CH_2Cl_2$ to give the title compound as slightly yellow oil.

MS: m/z 230 (M+H).

EXAMPLE 15

2,2-Dimethyl-3-(4-pyridin-3-yl-imidazol-1-yl)-propyl acetate

To a solution of 4-pyridin-3-yl-imidazole (50 mg) in DMSO (methyl sulfoxide) (1.7 mL) was added powered KOH (57 mg) and 3-bromo-2,2-dimethylpropyl acetate and the resulting suspension was heated at 70° C. for 48 hours. Water was added followed by $CHCl_3$, the aqueous layer was extracted with $CHCl_3$, the combined organic layers were washed with brine, dired over $Na_2SO_4$ and evaporated in vacuo. The redisue was purified by preparative TLC (10% MeOH-90% $CH_2Cl_2$) the title compound as slightly yellow oil.

MS: m/z 274 (M+H).

EXAMPLE 16

2,2-Dimethyl-3-(4-pyridin-3-yl-imidazol-1-yl)-propanol

To a solution of 2,2-Dimethyl-3-(4-pyridin-3-yl-imidazol-1-yl)-propyl acetate (20 mg) in methanol was added saturated solution of $K_2CO_3$ in metanol (1.5 mL) and the resulting solution was stirred at room temperature for 1 hour. MeOH was evaporated in vacuo and water was added followed by $CH_2Cl_2$. The aqueous layer was extracted with $CHCl_3$, the combined organic layers were washed with brine, dired over $Na_2SO_4$ and evaporated in vacuo to afford the title compound as a slightly yellow oil.

MS: m/z 232 (M+H).

EXAMPLE 17

2,2-Dimethyl-3-(4-pyridin-3-yl-imidazol-1-yl)-propioaldehyde

To a solution of 2,2-Dimethyl-3-(4-pyridin-3-yl-imidazol-1-yl)-propanol (11 mg) in $CH_2Cl_2$ was added Dess-Martin periodinane (41 mg) and the resulting solution was stirred at room temperature for 15 minutes. Saturated $NaHCO_3$ was added, the aqueous layer was extracted with $CHCl_3$, the combined organic layers were washed with brine, dired over $Na_2SO_4$ and evaporated in vacuo to afford the title compound as a slightly yellow oil.

MS: m/z 230 (M+H).

EXAMPLE 18

11-Deoxy-5-O-desosaminyl-11-(2,2-dimethyl-3-(4-pyridin-3-yl-imidazol-1-yl-propyl))hydrazo-6-O-methyl-3-oxoerythronolide A, 11,12-carbamate, 9-E-(O-methyl)oxime To a solution of 11-deoxy-5-O-desosaminyl-11-hydrazo-6-O-methyl-3-oxoerythronolide A, 11,12-carbamate, 9-E-(O-methyl)oxime (24 mg) and 2,2-dimethyl-3-(4-pyridin-3-yl-imidazol-1-yl)-propioaldehyde (10 mg) in toluene (0.36 mL) was added acetic acid (6 uL) and the resulting solution was heated at 70° C. for 24 hours. Toluene was evaporated in vacuo and the residue was then dissolved in methanol (0.36 mL). Acetic acid (20 uL) was added to the above solution followed by $NaBH_3CN$ (5 mg), and the resulting solution was stirred at room temperature for 1 hour. Saturated $NaHCO_3$ was added followed by $CH_2Cl_2$. Added. The aqueous layer was extracted with $CH_2Cl_2$ (3 times), the combined organic layers were washed with brine, dried over anhydrous $MgSO_4$, and concentrated in vacuo. The crude product was purified by preparative TLC (10% MeOH-1% $NH_3.H_2O$-89% $CH_2Cl_2$) to afford the title compound as a white solid.

$^1$H NMR ($CDCl_3$, 400 MHz) δ3.63 (3H, s), 2.65 (3H, s), 2.28 (6H, s), 1.44 (3H, s), (3H, s), 1.30 (3H, d, J=6.8 Hz), 1.25 (3H, d, J=7.6 Hz), 1.21 (3H, d, J=6.0 Hz), 1.11 (3H, d, J=7.2 Hz), 1.02 (3H, s), 0.97 (3H, d, J 7.2 Hz), 0.94 (3H, s), 0.74 (3H, t, J=7.6 Hz).

MS: m/z 870 (M+H).

EXAMPLE 19

11-Deoxy-5-O-desosaminyl-11-(2-methyl-3-(4-pyridin-3-yl-imidazol-1-yl-propyl))hydrazo-6-O-methyl-3-oxoerythronolide A, 11,12-carbamate, 9-E-(O-methyl)oxime To a solution of 11-deoxy-5-O-desosaminyl-11-hydrazo-6-O-methyl-3-oxoerythronolide A, 11,12-carbamate, 9-E-(O-methyl)oxime (2.8 g) and 2-methyl-3-(4-pyridin-3-yl-imidazol-1-yl)-propioaldehyde (1.0 g) in toluene (0.36 mL) was added acetic acid (0.24 mL) and the resulting solution was heated at 70° C. for 24 hours. Toluene was evaporated in vacuo and the residue was then dissolved in methanol (20 mL). Acetic acid (2.44 mL) was added to the above solution followed by $NaBH_3CN$ (1.83 g), and the resulting solution was stirred at room temperature for 1 hour. Saturated $NaHCO_3$ was added followed by $CH_2Cl_2$. Added. The aqueous layer was extracted with $CH_2Cl_2$ (3 times), the combined organic layers were washed with brine, dried over anhydrous $MgSO_4$, and concentrated in vacuo. The crude product was purified by preparative HPLC by using Kromasil C18 column and 35% acetonitrile/64% 15 mM ammonium acetate/1% trifluroacetic acid to give two isomers of the title compound.

One isomer: $^1$H NMR ($CDCl_3$, 400 MHz) δ3.71 (3H, s), 2.71 (3H, s), 2.25 (6H, s), 1.45 (3H, s), 1.39 (3H, s), 1.34 (3H, d, J=6.8 Hz), 1.28 (3H, d, J=7.6 Hz), 1.22 (3H, d, J=6.0 Hz), 1.10 (3H, d, J=6.8 Hz), 1.06 (3H, d, J=6.8 Hz), 0.98 (3H, d, J=6.8 Hz), 0.81 (3H, t, J=7.2 Hz).

Another isomer: $^1$H NMR ($CDCl_3$, 400 MHz) δ3.73 (3H, s), 2.67 (3H, s), 2.25 (6H, s), 1.47 (3H, s), 1.38 (3H, s), 1.30 (3H, d, J=6.8 Hz), 1.27 (3H, d, J=7.2 Hz), 1.22 (3H, d, J=6.0 Hz), 1.13 (3H, d, J=6.8 Hz), 0.99 (3H, d, J=6.8 Hz), 0.96 (3H, d, J=6.8 Hz), 0.81 (3H, t, J=6.8 Hz).

EXAMPLE 20

11-Deoxy-5-O-desosaminyl-11-(3,3-dimethyl-3-(4-pyridin-3-yl-imidazol-1-yl-propyl))hydrazo-6-O-methyl-3-oxoerythronolide A, 11.12-carbamate, 9-E-(O-methyl)oxime To a solution of 11-deoxy-5-O-desosaminyl-11-hydrazo-6-O-methyl-3-oxoerythronolide A, 11,12-carbamate, 9-E-(O-methyl)oxime (257 mg) and 3,3-dimethyl-3-(4-pyridin-3-yl-imidazol-1-yl)-propioaldehyde (200 mg) in toluene (1.9 mL) was added acetic acid (0.09 mL) and the resulting solution was heated at room temperature for 24 hours. Toluene was evaporated in vacuo and the residue was then dissolved in methanol (2.6 mL). Acetic acid (0.3 mL) was added to the above solution followed by $NaBH_3CN$ (49 mg), and the resulting solution was stirred at room temperature for 1 hour. Saturated $NaHCO_3$ was added followed by $CH_2Cl_2$. Added. The aqueous layer was extracted with $CH_2Cl_2$ (3 times), the combined organic layers were washed with brine, dried over anhydrous $MgSO_4$, and concentrated in vacuo. The crude product was purified by preparative TLC (10% MeOH-1% $NH_3.H_2O$-89% $CH_2Cl_2$) to afford the title compound as a white solid.

$^1$H NMR ($CDCl_3$, 400 MHz) δ3.61 (3H, s), 2.55 (3H, s), 2.32 (6H, s), 1.62 (3H, s), 1.60 (3H, s), 1.42 (3H, s), 1.32 (3H, d, J=6.8 Hz), 1.30 (3H, s), 1.24 (3H, d, J=7.6 Hz), 1.21 (3H, d, J=5.6 Hz), 1.02 (3H, J=7.2 Hz), 0.93 (3H, d, J=6.8 Hz), 0.81 (3H, t, J=7.2 Hz).

MS: m/z 870 (M+H).

EXAMPLE 21

2-Methyl-3-(4-pyridin-3-yl-imidazol-1-yl)-propioaldehyde

To a solution of 4-pyridin-3-yl-imidazole (8.5 g) in THF (293 mL) was added acetic acid (16.8 mL) and methacrolein (9.7 mL) and the resulting solution was heated under gentle reflux for 24 hours. Another 9.7 mL methacrolein was added and the solution was heated under reflux for another 24 hours. THF was then removed in vacuo and the residue was purified on a Flash 75 long column eluting with MeOH—$CH_2Cl_2$ to give the title compound as slightly yellow oil.

MS: m/z 215 (M+H).

EXAMPLE 22

2,2-Dimethyl-3-(4-pyridin-3-yl-imidazol-1-yl)-propyl acetate

To a solution of 4-pyridin-3-yl-imidazole (50 mg) in DMSO (1.7 mL) was added powered KOH (57 mg) and 3-bromo-2,2-dimethylpropyl acetate and the resulting suspension was heated at 70° C. for 48 hours. Water was added followed by CHCl$_3$, the aqueous layer was extracted with CHCl$_3$, the combined organic layers were washed with brine, dired over Na$_2$SO$_4$ and evaporated in vacuo. The residue was purified by preparative TLC (10% MeOH-90% CH$_2$Cl$_2$) the title compound as slightly yellow oil.

MS: m/z 274 (M+H).

EXAMPLE 23

2,2-Dimethyl-3-(4-pyridin-3-yl-imidazol-1-yl)-propanol

To a solution of 2,2-Dimethyl-3-(4-pyridin-3-yl-imidazol-1-yl)-propyl acetate (20 mg) in methanol was added saturated solution of K$_2$CO$_3$ in metanol (1.5 mL) and the resulting solution was stirred at room temperature for 1 hour. MeOH was evaporated in vacuo and water was added followed by CH$_2$Cl$_2$. The aqueous layer was extracted with CHCl$_3$, the combined organic layers were washed with brine, dried over Na$_2$SO$_4$ and evaporated in vacuo to afford the title compound as a slightly yellow oil.

MS: m/z 232 (M+H).

EXAMPLE 24

2,2-Dimethyl-3-(4-pyridin-3-yl-imidazol-1-yl)-propioaldehyde

To a solution of 2,2-Dimethyl-3-(4-pyridin-3-yl-imidazol-1-yl)-propanol (11 mg) in CH$_2$Cl$_2$ was added Dess-Martin periodinane (41 mg) and the resulting solution was stirred at room temperature for 15 minutes. Saturated NaHCO$_3$ was added, the aqueous layer was extracted with CHCl$_3$, the combined organic layers were washed with brine, dried over Na$_2$SO$_4$ and evaporated in vacuo to afford the title compound as a slightly yellow oil.

MS: m/z 230 (M+H).

EXAMPLE 25

11-Deoxy-5-O-desosaminyl-11-(2,2-dimethyl-3-(4-pyridin-3-yl-imidazol-1yl)-propyl)hydrazo-6-O-methyl-3-oxoerythronolide A, 11,12-carbamate, 9-E-(O-methyl)oxime To a solution of 11-deoxy-5-O-desosaminyl-11-hydrazo-6-O-methyl-3-oxoerythronolide A, 11,12-carbamate, 9-E-(O-methyl)oxime (24 mg) and 2,2-dimethyl-3-(4-pyridin-3-yl-imidazol-1-yl)-propioaldehyde (10 mg) in toluene (0.36 mL) was added acetic acid (6 uL) and the resulting solution was heated at 70° C. for 24 hours. Toluene was evaporated in vacuo and the residue was then dissolved in methanol (0.36 mL). Acetic acid (20 uL) was added to the above solution followed by NaBH$_3$CN (5 mg), and the resulting solution was stirred at room temperature for 1 hour. Saturated NaHCO$_3$ was added followed by CH$_2$Cl$_2$. Added. The aqueous layer was extracted with CH$_2$Cl$_2$ (3 times), the combined organic layers were washed with brine, dried over anhydrous MgSO$_4$, and concentrated in vacuo. The crude product was purified by preparative TLC (10% MeOH-1% NH$_3$.H$_2$O-89% CH$_2$Cl$_2$) to afford the title compound as a white solid.

$^1$H NMR (CDCl$_3$, 400 MHz) δ3.63 (3H, s), 2.65 (3H, s), 2.28 (6H, s), 1.44 (3H, s), 1.34 (3H, s), 1.30 (3H, d, J=6.8 Hz), 1.25 (3H, d, J=7.6 Hz), 1.21 (3H, d, J=6.0 Hz), 1.11 (3H, d, J=7.2 Hz), 1.02 (3H, s), 0.97 (3H, d, J 7.2 Hz), 0.94 (3H, s), 0.74 (3H, t, J=7.6 Hz).

MS: m/z 870 (M+H).

EXAMPLE 26

11-Deoxy-5-O-desosaminyl-11-(2-methyl-3-(4-pyridin-3-yl-imidazol-1-yl)-propyl)hydrazo-6-O-methyl-3-oxoerythronolide A, 11,12-carbamate, 9-E-(O-methyl)oxime To a solution of 1-deoxy-5-O-desosaminyl-11-hydrazo-6-O-methyl-3-oxoerythronolide A, 11,12-carbamate, 9-E-(O-methyl)oxime (2.8 g) and 2-methyl-3-(4-pyridin-3-yl-imidazol-1-yl)-propioaldehyde (1.0 g) in toluene (0.36 mL) was added acetic acid (0.24 mL) and the resulting solution was heated at 70° C. for 24 hours. Toluene was evaporated in vacuo and the residue was then dissolved in methanol (20 mL). Acetic acid (2.44 mL) was added to the above solution followed by NaBH$_3$CN (1.83 g), and the resulting solution was stirred at room temperature for 1 hour. Saturated NaHCO$_3$ was added followed by CH$_2$Cl$_2$. The aqueous layer was extracted with CH$_2$Cl$_2$ (3 times), the combined organic layers were washed with brine, dried over anhydrous MgSO$_4$, and concentrated in vacuo. The crude product was purified by preparative HPLC by using a Kromasil C18 column and 35% acetonitrile/64% 15mM ammonium acetate/1% trifluroacetic acid to give two isomers of the title compound.

One isomer: $^1$H NMR (CDCl$_3$, 400 MHz) δ3.71 (3H, s), 2.71 (3H, s), 2.25 (6H, s), 1.45 (3H, s), 1.39 (3H, s), 1.34 (3H, d, J=6.8 Hz), 1.28 (3H, d, J=7.6 Hz), 1.22 (3H, d, J=6.0 Hz), 1.10 (3H, d, J=6.8 Hz), 1.06 (3H, d, J=6.8 Hz), 0.98 (3H, d, J=6.8 Hz), 0.81 (3H, t, J=7.2 Hz).

Second isomer: $^1$H NMR (CDCl$_3$, 400 MHz) δ3.73 (3H, s), 2.67 (3H, s), 2.25 (6H, s), 1.47 (3H, s), 1.38 (3H, s), 1.30 (3H, d, J=6.8 Hz), 1.27 (3H, d, J=7.2 Hz), 1.22 (3H, d, J=6.0 Hz), 1.13 (3H, d, J=6.8 Hz), 0.99 (3H, d, J=6.8 Hz), 0.96 (3H, d, J=6.8 Hz), 0.81 (3H, t, J=6.8 Hz).

Specific compounds that are part of the present invention and have been or can be made according to the methods provided above, include the following:

11-Deoxy-5-O-desosaminyl-11-(3,3-dimethyl-3-(4-pyridin-3-yl-imidazol-1-yl)-propyl)hydrazo-6-O-methyl-3-oxoerythronolide A, 11,12-carbamate, 9-E-(O-methyl)oxime;

11-Deoxy-5-O-desosaminyl-11-(3(R)-methyl-3-(4-pyridin-3-yl-imidazol-1-yl)-propyl)hydrazo-6-O-methyl-3-oxoerythronolide A, 11,12-carbamate, 9-E-(O-methyl)oxime;

11-Deoxy-5-O-desosaminyl-11-(3(R)-ethyll-3-(4-pyridin-3-yl-imidazol-1-yl)-propyl)hydrazo-6-O-methyl-3-oxoerythronolide A, 11,12-carbamate, 9-E-(O-methyl)oxime;

11-Deoxy-5-O-desosaminyl-11-(3(S)-methyl-3-(4-pyridin-3-yl-imidazol-1-yl)-propyl)hydrazo-6-O-methyl-3-oxoerythronolide A, 11,12-carbamate, 9-E-(O-methyl)oxime;

11-Deoxy-5-O-desosaminyl-11-(3(S)-ethyl-3-(4-pyridin-3-yl-imidazol-1-yl)-propyl)hydrazo-6-O-methyl-3-oxoerythronolide A, 11,12-carbamate, 9-E-(O-methyl)oxime;

11-Deoxy-5-O-desosaminyl-11-(2-(1-(4-pyridin-3-yl-imidazol-1-yl)-cyclopropyl)-ethyl)hydrazo-6-O-methyl-3-oxoerythronolide A, 11,12-carbamate, 9-E-(O-methyl)oxime;

11-Deoxy-5-O-desosaminyl-11-(2-(1-(4-pyridin-3-yl-imidazol-1-yl)-cyclobutyl)-ethyl)hydrazo-6-O-methyl-3-oxoerythronolide A, 11,12-carbamate, 9-E-(O-methyl)oxime;

11-Deoxy-5-O-desosaminyl-11-(2,2-dimethyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2,2-diethyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2,2-difluro-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2,2-dichloro-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2,2-dibromo-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(1-(4-pyridin-3-yl-imidazol-1-yl-methyl)-cyclopropyl)-methyl)hydrazo-4-O-methyl-3-oxoerythronolide A, 11,12-carbamate, 9-E-(O-methyl)oxime;

11-Deoxy-5-O-desosaminyl-11-(1-(4-pyridin-3-yl-imidazol-1-yl-methyl)-cyclobutyl)-methyl)hydrazo-6-O-methyl-3-oxoerythronolide A, 11,12-carbamate, 9-E-(O-methyl)oxime;

11-Deoxy-5-O-desosaminyl-11-(2(R)-methyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2(R)-ethyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2(S)-methyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2(S)-ethyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2(R)-fluro-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2(S)-flurol-3-(4-pyridin-3-yl-imidazol-1-yl)-propyl)hydrazo-6-O-methyl-3-oxoerythronolide A, 11,12-carbamate, 9-E-(O-methyl) oxime;

and the pharmaceutically acceptable salts, prodrugs and solvates of the foregoing compounds.

Specific compounds of the present invention include

11-Deoxy-5-O-desosaminyl-11-(2-(1-(4-pyridin-3-yl-imidazol-1-yl)-cyclopropyl)-ethyl)hydrazo-6-O-methyl-3-oxoerythronolide A, 11,12-carbamate, 9-E-(O-methyl) oxime;

11-Deoxy-5-O-desosaminyl-11-(2-(1-(4-pyridin-3-yl-imidazol-1-yl)-cyclobutyl)-ethyl)hydrazo-6-O-methyl-3-oxoerythronolide A, 11,12-carbamate, 9-E-(O-methyl) oxime;

11-Deoxy-5-O-desosaminyl-11-(2,2-dimethyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2,2-diethyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2,2-difluoro-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2,2-dichloro-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2,2-dibromo-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(1-(4-pyridin-3-yl-imidazol-1-yl-methyl)-cyclopropyl)-methyl)hydrazo-6-O-methyl-3-oxoerythronolide A, 11,12-carbamate, 9-E-(O-methyl)oxime;

11-Deoxy-5-O-desosaminyl-11-(1-(4-pyridin-3-yl-imidazol-1-yl-methyl)-cyclobutyl)-methyl)hydrazo-6-O-methyl-3-oxoerythronolide A, 11,12-carbamate, 9-E-(O-methyl)oxime;

11-Deoxy-5-O-desosaminyl-11-(2-(R)-methyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2-(R)-ethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2-(S)-methyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2-(S)-ethyl-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2-(R)-fluoro-3-(4-pyridin-3-yl-imidazol-1-yl)-propyl)hydrazo-6-O-methyl-3-oxoerythronolide A, 11,12-carbamate, 9-E-(O-methyl) oxime;

11-Deoxy-5-O-desosaminyl-11-(2-(S)-fluoro-3-(4-pyridin-3-yl-imidazol-1-yl-propyl))hydrazo-6-O-methyl-3-oxoerythronolide A, 11,12-carbamate, 9-E-(O-methyl) oxime;

and the pharmaceutically acceptable salts, prodrugs and solvates of the foregoing compounds.

What is claimed is:
1. A compound of the formula

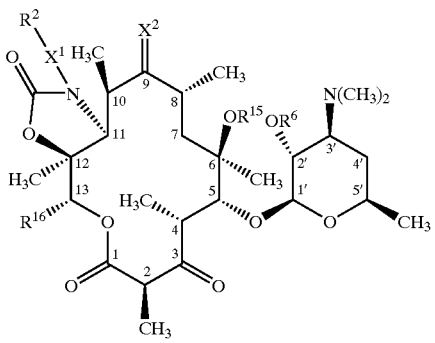

or a pharmaceutically acceptable salt or solvate thereof, wherein:
$X^1$ is O, —$CR^{13}R^{14}$— or —$NR^4$—;
$X^2$ is =O or =$NOR^1$;
$R^1$ is H, methyl or ethyl;
$R^2$ is —$C(R^7)(R^8)C(R^9)(R^{10})C(R^{11})(R^{12})$(4–10 membered heterocyclic) or —$(CR^7R^8)_r(C_3-C_7$ cycloalkylene)$(CR^9R^{10})_q$(4–10 membered heterocyclic), wherein q and r are each integers independently ranging from 0 to 2, and the heterocyclic moiety of the foregoing groups is substituted by —$(CR^4R^5)_t$(4–10 membered heterocyclic) or —$(CR^4R^5)t(C_6-C_{10}$ aryl) wherein t is an integer from 0 to 5, and the aryl and heterocyclic moieties of each of the foregoing groups are optionally substituted by 1 to 4 $R^3$ groups;
each $R^3$ is independently selected from the group consisting of halo, cyano, nitro, trifluoromethyl, trifluoromethoxy, azido, —$C(O)R^5$, —$C(O)OR^5$, —$OC(O)R^5$, —$NR^5C(O)R^4$, —$C(O)NR^4R^5$, —$NR^4R^5$, hydroxy, $C_1$–$C_6$ alkyl, $C_2$–$C_6$ alkenyl, $C_2$–$C_6$ alkynyl, $C_6$–$C_{10}$ aryl, 4–10 membered heterocyclic, and $C_1$–$C_6$ alkoxy;
each $R^4$ and $R^5$ is independently selected from H and $C_1$–$C_6$ alkyl;
$R^6$ is H or —$C(O)(C_1-C_6$ alkyl);
$R^7$, $R^8$, $R^9$, $R^{10}$, $R^{11}$, $R^{12}$, $R^{13}$ and $R^{14}$ are each independently selected from H, halo and $C_1$–$C_6$ alkyl, provided that (a) where $X^1$ is —$CR^{13}R^{14}$— and $R^2$ is —$C(R^7)(R^8)C(R^9)(R^{10})C(R^{11})(R^{12})$(4–10 membered heterocyclic), at least one of $R^7$, $R^8$, $R^9$, $R^{10}$, $R^{11}$, $R^{12}$, $R^{13}$ and $R^{14}$ is halo or $C_1$–$C_6$ alkyl, and (b) where $X^1$ is —$NR^4$— and $R^2$ is —$C(R^7)(R^8)C(R^9)(R^{10})C(R^{11})$($R^{12}$)(4–10 membered heterocyclic), at least one of $R^7$, $R^8$, $R^9$, $R^{10}$, $R^{11}$, and $R^{12}$ is halo or $C_1$–$C_6$ alkyl;
or $R^7$ and $R^8$ are taken together with the carbon to which each is attached to form a $C_3$–$C_7$ cycloalkyl group and $R^9$, $R^{10}$, $R^{11}$, $R^{12}$, $R^{13}$ and $R^{14}$ are each independently selected from H, halo and $C_1$–$C_6$ alkyl;
or $R^9$ and $R^{10}$ are taken together with the carbon to which each is attached to form a $C_3$–$C_6$ cycloalkyl group and $R^7$, $R^8$, $R^{11}$, $R^{12}$, $R^{13}$ and $R^{14}$ are each independently selected from H, halo and $C_1$–$C_6$ alkyl;
or $R^{11}$ and $R^{12}$ are taken together with the carbon to which each is attached to form a $C_3$–$C_7$ cycloalkyl group and $R^7$, $R^8$, $R^9$, $R^{10}$, $R^{13}$ and $R^{14}$ are each independently selected from H, halo and $C_1$–$C_6$ alkyl;

$R^{15}$ is $C_1$–$C_6$ alkyl; and
$R^{16}$ is H or $C_1$–$C_{10}$ alkyl.

2. A compound according to claim 1 wherein $X^2$ is =$NOR^1$, $R^{15}$ is methyl, $R^{16}$ is ethyl, $R^6$ is H or acetyl, $X^1$ is —$NR^4$— and $R^2$ is —$C(R^7)(R^8)C(R^9)(R^{10})C(R^{11})(R^{12})$ (4–10 membered heterocyclic) wherein said heterocyclic group is substituted by 4–10 membered heterocyclic and the foregoing heterocyclic moieties are optionally substituted by 1 or 2 substituents independently selected from halo and $C_1$–$C_3$ alkyl.

3. A pharmaceutical composition for the treatment of a disorder selected from a bacterial infection, a protozoal infection, and a disorder related to a bacterial infection or protozoal infection in a mammal, fish, or bird which comprises a therapeutically effective amount of a compound of claim 1 and a pharmaceutically acceptable carrier.

4. A method of treating a disorder selected from a bacterial infection, a protozoal infection, and a disorder related to a bacterial infection or protozoal infection in a mammal, fish, or bird which comprises administering to said mammal, fish or bird a therapeutically effective amount of a compound of claim 1.

5. A compound selected from the group consisting essentially of:

11-Deoxy-5-O-desosaminyl-11-(3,3-dimethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(3(R)-methyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(3(R)-ethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(3(S)-methyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(3(S)-ethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2-(1-(4-pyridin-3-yl-imidazol-1-yl)-cyclopropyl)-ethyl)hydrazo-6-O-methyl-3-oxoerythronolide A, 11,12-carbamate, 9-E-(O-methyl) oxime;

11-Deoxy-5-O-desosaminyl-11-(2-(1-(4-pyridin-3-yl-imidazol-1-yl)-cyclobutyl)-ethyl)hydrazo-6-O-methyl-3-oxoerythronolide A, 11,12-carbamate, 9-E-(O-methyl) oxime;

11-Deoxy-5-O-desosaminyl-11-(2,2-dimethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2,2-diethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2,2-difluro-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2,2-dichloro-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2,2-dibromo-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(1-(4-pyridin-3-yl-imidazol-1-yl-methyl)-cyclopropyl)-methyl-hydrazo-6-O-methyl-3-oxoerythronolide A, 11,12-carbamate, 9-E-(O-methyl)oxime;

11-Deoxy-5-O-desosaminyl-11-(1-(4-pyridin-3-yl-imidazol-1-yl-methyl)-cyclobutyl)-methyl-hydrazo-6-O-methyl-3-oxoerythronolide A, 11,12-carbamate, 9-E-(O-methyl)oxime;

11-Deoxy-5-O-desosaminyl-11-(2(R)-methyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2(R)-ethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2(S)-methyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2(S)-ethyl-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2(R)-fluro-3-(4-pyridin-3-yl-imidazol-1-yl-propyl))hydrazo-6-O-methyl-3-oxoerythronolide A, 11,12-carbamate, 9-E-(O-methyl) oxime;

11-Deoxy-5-O-desosaminyl-11-(2(S)-flurol-3-(4-pyridin-3-yl-imidazol-1-yl-propyl))hydrazo-6-O-methyl-3-oxoerythronolide A, 11,12-carbamate, 9-E-(O-methyl) oxime;

and the pharmaceutically acceptable salts and solvates of the foregoing compounds.

6. A compound of the formula

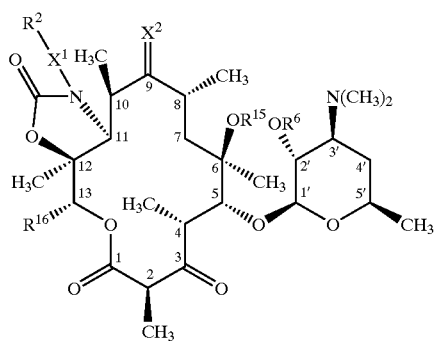

or a pharmaceutically acceptable salt or solvate thereof, wherein:

$X^1$ is O, —$CR^{13}R^{14}$— or —$NR^4$—;

$X^2$ is =O or =$NOR^1$;

$R^1$ is H, methyl or ethyl;

$R^2$ is —$C(R^7)(R^8)C(R^9)(R^{10})C(R^{11})(R^{12})$(4-pyridin-3-yl-imidazol-1-yl)

$R^6$ is H or —$C(O)(C_1-C_6$ alkyl);

$R^7$, $R^8$, $R^9$, $R^{10}$, $R^{11}$, $R^{12}$, $R^{13}$ and $R^{14}$ are each independently selected from H, halo and $C_1-C_6$ alkyl, provided that (a) where $X^1$ is —$CR^{13}R^{14}$— and $R^2$ is —$C(R^7)(R^8)C(R^9)(R^{10})C(R^{11})(R^{12})$(4–10 membered heterocyclic), at least one of $R^7$, $R^8$, $R^9$, $R^{10}$, $R^{11}$, $R^{12}$, $R^{13}$ and $R^{14}$ is halo or $C_1-C_6$ alkyl, and (b) where $X^1$ is —$NR^4$— and $R^2$ is —$C(R^7)(R^8)C(R^9)(R^{10})C(R^{11})(R^{12})$(4–10 membered heterocyclic), at least one of $R^7$, $R^8$, $R^9$, $R^{10}$, $R^{11}$, and $R^{12}$ is halo or $C_1-C_6$ alkyl;

or $R^7$ and $R^8$ are taken together with the carbon to which each is attached to form a $C_3-C_7$ cycloalkyl group and $R^9$, $R^{10}$, $R^{11}$, $R^{12}$, $R^{13}$ and $R^{14}$ are each independently selected from H, halo and $C_1-C_6$ alkyl;

or $R^9$ and $R^{10}$ are taken together with the carbon to which each is attached to form a $C_3-C_6$ cycloalkyl group and $R^7$, $R^8$, $R^{11}$, $R^{12}$, $R^{13}$ and $R^{14}$ are each independently selected from H, halo and $C_1-C_6$ alkyl;

or $R^{11}$ and $R^{12}$ are taken together with the carbon to which each is attached to form a $C_3-C_7$ cycloalkyl group and $R^7$, $R^8$, $R^9$, $R^{10}$, $R^{13}$ and $R^{14}$ are each independently selected from H, halo and $C_1-C_6$ alkyl;

$R^{15}$ is $C_1-C_6$ alkyl; and $R^{16}$ is H or $C_1-C_{10}$ alkyl.

7. A compound according to claim 6, wherein $X^1$ is —NH— and $R^2$ is —$C(R^7)(R^8)C(R^9)(R^{10})C(R^{11})(R^{12})$(4-pyridin-3-yl-imidazol-1-yl).

8. A compound according to claim 7 wherein $R^7$, $R^8$, $R^9$ and $R^{10}$ are each H, $R^{11}$ is methyl or ethyl, and $R^{12}$ is H, methyl or ethyl.

9. A compound according to claim 7 wherein $R^7$, $R^8$, $R^{11}$ and $R^{12}$ are each H, $R^9$ is methyl or ethyl, and $R^{10}$ is H, methyl or ethyl.

10. A compound according to claim 7 wherein $R^9$, $R^{10}$, $R^{11}$ and $R^{12}$ are each H, $R^7$ is methyl or ethyl, and $R^8$ is H, methyl or ethyl.

* * * * *